United States Patent [19]
Imonti

[11] Patent Number: 4,674,502
[45] Date of Patent: Jun. 23, 1987

[54] INTRAOCULAR SURGICAL INSTRUMENT

[75] Inventor: Maurice M. Imonti, Dana Point, Calif.

[73] Assignee: CooperVision, Inc., Menlo Park, Calif.

[21] Appl. No.: 780,814

[22] Filed: Sep. 27, 1985

[51] Int. Cl.$^4$ .............................................. A61F 17/32
[52] U.S. Cl. ..................................... 128/305; 604/22; 128/752; 128/750; 128/751
[58] Field of Search ............... 128/305, 310, 311, 319, 128/306, 305.1, 751, 752, 753, 754, 755, 749, 750; 604/22

[56] References Cited
U.S. PATENT DOCUMENTS 4,200,106 4/1980 Douvas et al. ...................... 128/305
4,577,629 2/1986 Martinez .............................. 128/305

FOREIGN PATENT DOCUMENTS 8101363 5/1981 PCT Int'l Appl. .

Primary Examiner—Henry A. Bennet
Attorney, Agent, or Firm—Vorys, Sater, Seymour & Pease

[57] ABSTRACT

An intraocular surgical instrument includes an elongated inner tube that is axially movably connected at a first end to a handpiece, and comprises a cutting edge at a distal end. An elongated outer tube is disposed coaxially with the inner tube, is connected at a first end to the handpiece, and includes a cutting edge at a distal end. A first clearance is provided between the inner tube and the outer tube at a first rearward region and a second region adjacent to the cutting edges, such that the cutting edges are maintained in a cutting relationship. A second clearance, larger than the first clearance, is provided at a third region disposed between the first and second regions.

35 Claims, 20 Drawing Figures

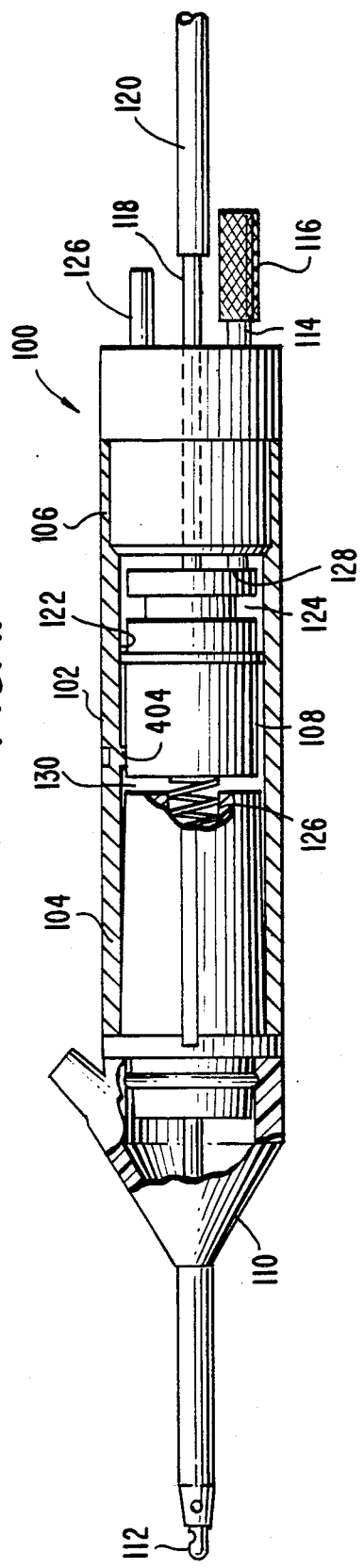
FIG. I.
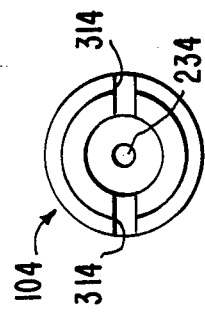
FIG. 3(c).
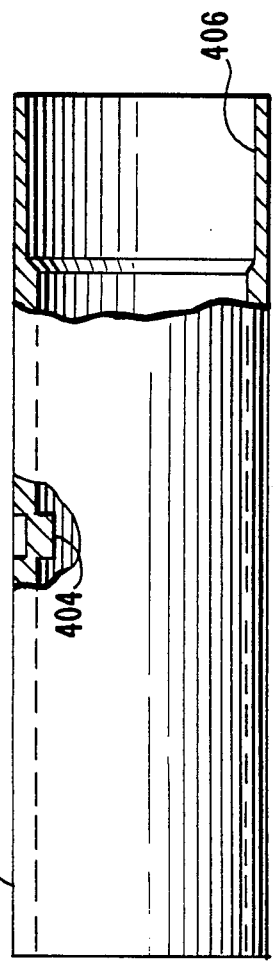
FIG. 4(b).
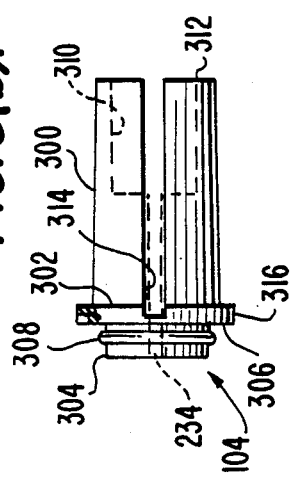
FIG. 3(b).
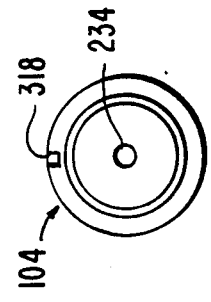
FIG. 3(a).
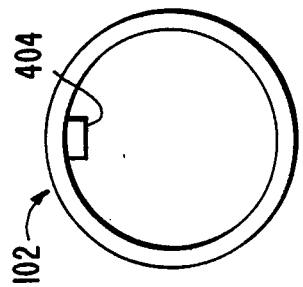
FIG. 4(a).

INTRAOCULAR SURGICAL INSTRUMENT

BACKGROUND OF THE INVENTION

This invention relates to intraocular surgical instruments and more particularly to instruments adapted to vitrectomy surgery that incorporate reciprocating cutters.

It is sometimes necessary to surgically remove a portion of the vitreous body of the eye in order to eliminate opaque regions of the body, blood, retinal tissue and the like. The vitreous body has a jelly-like consistency, requiring that portions to be excised be cleanly cut off from the remaining portion of the vitreous body. One method of severing vitreous portions involves the use of a surgical instrument that comprises coaxial slender tubes and which is inserted into the region of the vitreous to be removed. The outer tube has an orifice with a sharp cutting edge on the internal surface of the tube, while the inner tube has a sharp cutting edge formed on its outer periphery. The portion of the vitreous body to be excised is pulled into the orifice in the outer tube by suction applied to the inner tube, and the portion is severed by moving the cutting edge of the inner tube past the cutting edge of the outer tube in a reciprocating fashion.

It is important that the cutting edges of the reciprocating tubes of such instruments fit together closely in order to provide a good cutting action. If the cutting edges do not cooperate properly, there is a danger that a portion of the vitreous body might become trapped between the outer wall of the inner tube and the inner wall of the outer tube. This is a serious problem because tissue that becomes trapped is difficult to cut cleanly away from the remaining vitreous body, and further movement of the instrument may cause tension on the vitreous body that may damage the retina.

Various means have been provided for effecting the proper orientation of the cutting edges of the inner and outer tubes in order to clearly sever the portion of vitreous body to be removed. In most of the prior art devices, this objective is addressed by providing minimal clearance between the internal wall of the outer cutter tube and the external wall of the inner cutter tube along the entire length of their adjacency. While this arrangement helps to ensure the proper orientation of the tubes at the point where the cutting edges meet, it has caused a considerable amount of friction between the two walls.

In an attempt to overcome the problem of friction while retaining a proper alignment at the cutting edges, a longitudinal portion of the outer tube has been cut away between its two ends, as disclosed in U.S. Pat. No. 4,246,902, issued to Martinez. In this fashion, the friction that would have otherwise occurred between the cut-away portion and the inner tube is of course eliminated, but the amount of friction caused by movement of the remaining portions against the inner tube is maintained, and the lessened structural integrity caused by the removal may also be a source of problems. In particular, the cutting away of a large longitudinal portion of one of the cutting tubes may increase the flexibility of that tube to an extent that the precise orientation of the cutting edges is lost.

In addition, prior art devices of this type are generally manufactured in a way that increases the cost of the devices and causes disposability after a single use to be impractical. For example, in U.S. Pat. No. 4,246,902, the device is generally complex and requires a number of threaded parts.

SUMMARY OF THE INVENTION

It is thus an object of the present invention to provide an intraocular surgical instrument adapted for vitrectomy surgery that incorporates a reciprocating cutter, wherein cutting edges of inner and outer tubes are precisely aligned in order to provide optimum cutting of a portion of the vitreous body.

It is a further object of the invention to reduce the amount of friction between the internal surface of the outer cutter tube and the external surface of the inner cutter tube of a reciprocating vitreous cutter.

It is a further object of the present invention to provide a vitrectomy instrument that is easily and inexpensively manufactured, such that the instrument is disposable after a single use.

In accordance with the present invention, these objects, and others that will become apparent from the following, are met by the provision of an intraocular surgical instrument that includes an elongated inner tube that is axially movably connected at a first end to a handpiece and that comprises a cutting edge at a distal end. An elongated outer tube is disposed coaxially with the inner tube, is connected at a first end to the handpiece, and includes a cutting edge at a distal end. A first clearance is provided between the inner tube and the outer tube at a first rearward region and a second region adjacent to the cutting edges, such that the cutting edges are maintained in a cutting relationship. A second clearance, larger than the first clearance, is provided at a third region disposed between the first and second regions.

BRIEF DESCRIPTION OF THE DRAWINGS

FIG. 1 is an elevational side view of the intraocular surgical instrument in accordance with the present invention, partially shown in section.

FIG. 3 consists of detailed views of the front cap of the instrument of FIG. 1, FIG. 3(a) being a front view, FIG. 3(b) being a side view, and FIG. 3(c) being a rear view.

FIG. 4 consists of detailed views of the barrel of the instrument of FIG. 1, FIG. 4(a) being a front view and FIG. 4(b) being a side view, partially in section.

DETAILED DESCRIPTION OF THE PREFERRED EMBODIMENT

Figure 2:
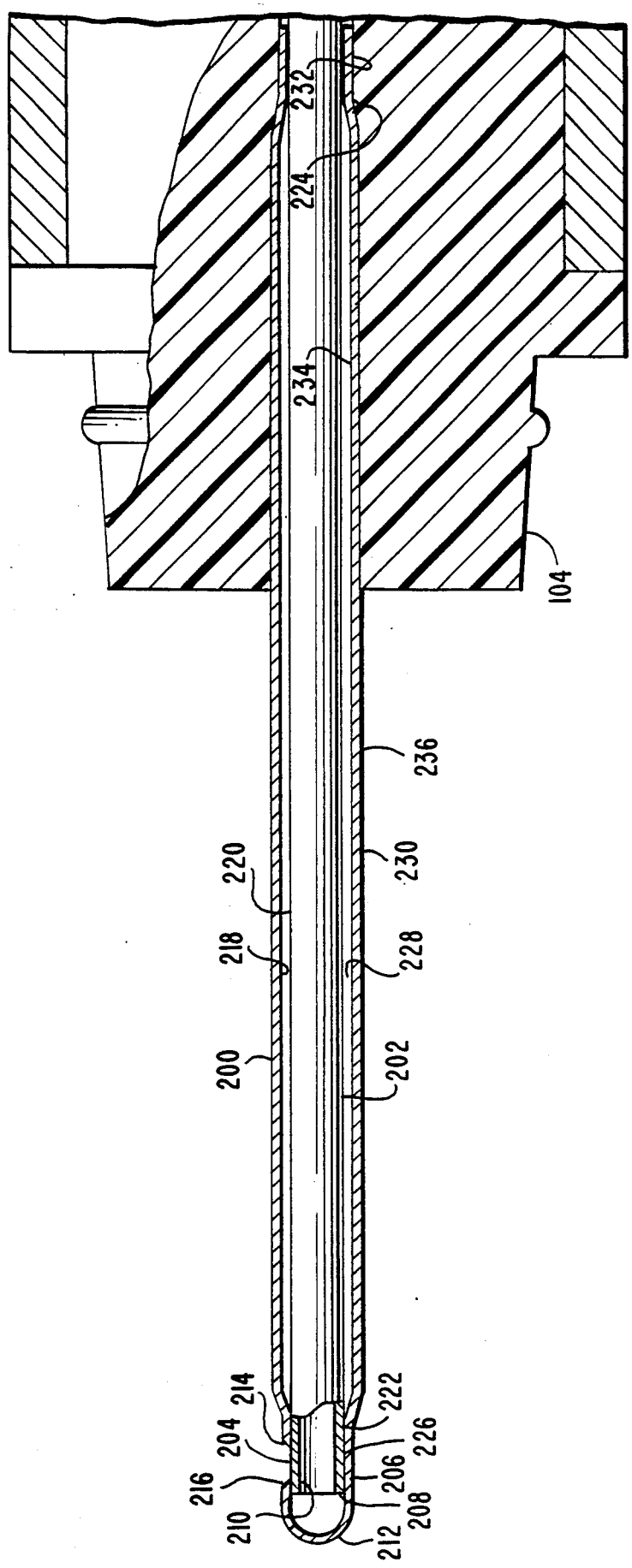
FIG. 2 is a detailed view of the cutter elements of the instrument of FIG. 1, partially in section.

As depicted generally in FIG. 1, the intraocular surgical instrument 100 of the present invention comprises a cylindrical barrel 102 that is enclosed at a front end with front cap 104 and at a rear end with rear cap 106. Piston 108 is disposed within the barrel between front cap 104 and rear cap 106 and a removable tip cap and sleeve assembly 110 is connected to a front surface of the front cap. Cutter assembly 112 is mounted onto a handpiece comprising barrel 102 and the parts that it holds. "Handpiece" as used herein generally refers to any apparatus onto which the cutter assembly is mounted.

The cutter assembly is detailed in FIG. 2, wherein it is seen that it comprises an outer cutter tube 200 and an inner cutter tube 202. The inner cutter tube is coaxial with the outer cutter tube and is able to slide in a reciprocating fashion within the outer tube.

Both of the tubes are connected at one of their respective ends to the handpiece, and distal end 204 of the inner tube and distal end 206 of the outer tube are provided with respective cutting edges. Cutting edge 208 of the inner tube is disposed at a distal tip of the tube. It is annular in shape and defines an opening 210 through which suction is applied. In a typical embodiment, inner tube 202 is made from a 23-gauge stainless steel tube having an external diameter of 0.025 inches.

Distal end 206 of outer tube 200 is closed at distal tip 212, and cutting orifice 214 is defined within the distal end. The cutting orifice is circular and comprises cutting edge 216 which is typically ground at an angle of about 45. As will be seen, inner tube 202 is caused to reciprocate in an axially directed fashion such that cutting edge 208 of the inner tube slides across cutting edge 216 of the outer tube. Outer tube 200 is typically made of stainless steel or the like, such as 20-gauge stainless steel tubing having an external diameter of 0.035 inches and an internal diameter of 0.027 inches.

An important feature of the present invention involves the amount of clearance provided between internal wall 218 of the outer tube and external wall 220 of the inner tube. A first clearance 222 is provided between the two walls at a first rearward region 224 adjacent to the handpiece and a second region 226 that is adjacent to the cutting edges. A second clearance 228 is provided in a third region 230 that extends between first region 224 and second region 226.

First clearance 222 is selected such that inner tube 202 is snugly retained within outer tube 200. The close fit in second region 226 provides a tight meshing of cutting edges 208 and 216, and the close fit in first region 224 further assures a proper alignment of the edges. The clearance in these regions is typically about 0.00025 inches. In the depicted preferred embodiment, first region 224 is disposed at one end 232 of the outer tube, but the positioning of the first region at other points rearward of third region 228 to achieve the beneficial results is within the scope of the invention.

At third region 228, the diameters of the interior wall 218 of the outer tube and exterior wall 220 of the inner tube are selected so that an increased clearance is achieved. The increased clearance is provided throughout most of the length of the outer tube and results in a relatively low friction between the walls of the tubes.

The increased clearance is typically selected from the range of 0.002 to 0.003 inches. In a preferred embodiment, as depicted in FIG. 2, the different clearances are provided by swaging outer tube 200 at regions 224 and 226, but other means for providing the first and second clearances, as for example by reducing the diameter of exterior wall 220 of the inner tube along the third region, are also within the scope of the invention.

The instrument of the present invention is manufactured easily and inexpensively with press-fitting parts and is disposable after a single use. As depicted in FIG. 2, outer tube 200 is retained within front cap 104 by press fitting. The front cap is molded from a synthetic resin such as acrylonitrile-butadiene-styrene resin (ABS) and defines a radially distensible axial bore 234 having a diameter slightly smaller than the diameter of outer wall 236 of outer tube 200. In this fashion, outer tube 200 is connected to front cap 104 by press fitting a portion of the tube into the cap, whereupon a slight pressure exerted by the axial bore against the outer tube retains the outer tube in position.

Front cap 104 is depicted in greater detail in FIG. 3. The front cap is provided with a generally cylindrical wall 300, a collar 302 disposed forwardly of the wall, and a stem 304 disposed on a front surface 306 of the collar. Annular boss 308 is provided on stem 304 and spring chamber 310 is defined within rear surface 312. Exhaust ports 314 extend from surface 312 on either side of spring chamber 310, pass longitudinally along wall 300, and exit at an outer surface 316 of collar 302. Front surface 306 defines a recess 318 for engaging tip cap and sleeve assembly 110.

Wall 300 of the front cap is slightly tapered, having a lesser diameter at the region of rear surface 312 than at a forward region adjacent to collar 302. The diameter in the region adjacent to the collar is slightly larger than an interior diameter of barrel 102, and the diameter in the region of surface 312 is less than the internal diameter of the barrel. In this way, the angle of wall 300 facilitates the entry of the rear end of the front cap into the front end of the barrel, and the engagement of the front cap to the barrel is provided by an interference fit. Axial bore 234 is integrally molded within the cap and serves as a mounting and guiding means for the cutting elements as depicted in FIG. 2.

Cylindrical barrel 102 is depicted in more detail in FIG. 4. The barrel is made of metal and preferrably from an extruded aluminum tube. Wall 402 is provided in one embodiment with a key 404 that protrudes interiorly. If desired, a bore 406 is provided for receiving end cap 106. Since the barrel serves as a handpiece, it is typically provided with a diamond knurl to facilitate gripping.

Rear cap 106 is, like front cap 104, molded from a synthetic resin such as ABS and is dimensioned to provide an interference fit within the rear end of barrel 102. In the embodiment illustrated in FIG. 5, the end cap is thus provided with a wall 500 that is tapered toward its front surface 502. Because of a reduced dimension of wall 500 in the area of surface 502, the end cap is easily inserted within the barrel. A collar 504 is also provided, and when end cap 106 is inserted such that collar 504 abuts wall 402 of the barrel, an interference fit is achieved by virtue of the increased diameter of the rearward region of wall 500 adjacent to the collar.

Figure 5A:
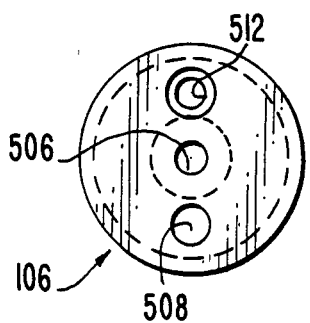
FIG. 5 consists of detailed views of the rear cap of the instrument of FIG. 1, FIG. 5(a) being a front view and FIG. 5(b) being a side view, partially in section.
Figure 5B:
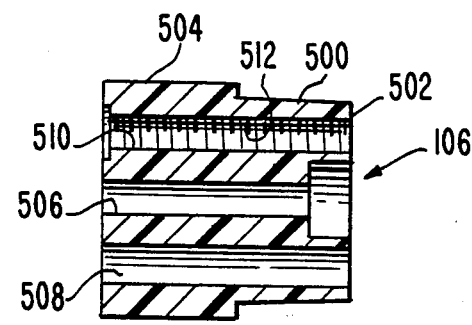

The end cap defines three bores as depicted in FIG. 5. Axial bore 506 is integrally molded within the cap and serves as a guiding means for inner tube 202. As depicted in FIG. 1, rear end 118 of inner tube 202 extends through the rear cap and is attached to flexible tube 120, which is connected to a source of suction in order to remove severed portions of vitreous. A second bore 508 serves as an inlet that is connected through conduit 126 to a source of pressurized gas for driving the piston in a forward direction. Bore 510 includes threads 512 for receiving an adjustment screw 114 having a knurled end 116.

Figure 6A:
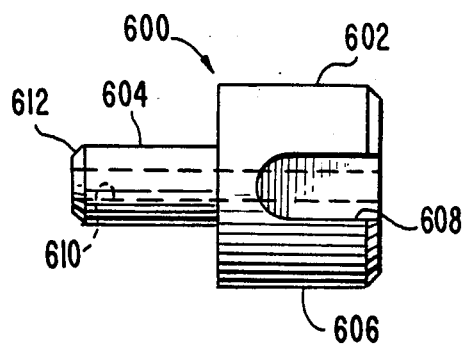
FIG. 6 consists of detailed views of a male part of the piston of the instrument of FIG. 1, FIG. 6(a) being a side view and FIG. 6(b) being a front view.
Figure 6B:
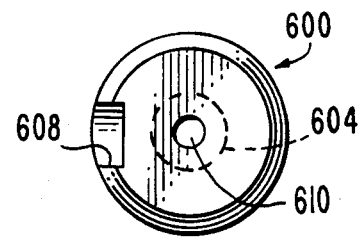
Figure 7A:
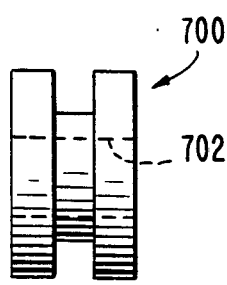
FIG. 7 consists of detailed views of a female part of the piston of the instrument of FIG. 1, FIG. 7(a) being a side view and FIG. 7(b) being a front view.
Figure 7B:
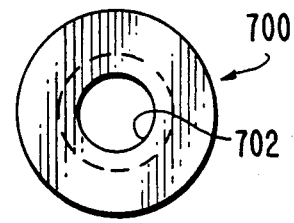
Figure 8A:
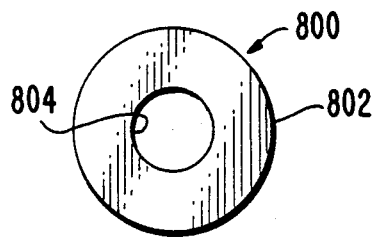
FIG. 8 consists of detailed views of a washer used in the piston of the instrument of FIG. 1, FIG. 8(a) being a top view and FIG. 8(b) being a side view.
Figure 8B:
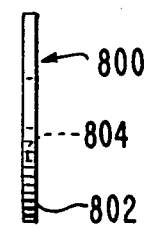
Figure 9A:
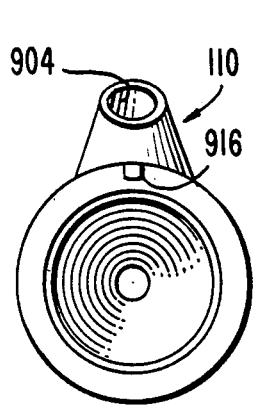
FIG. 9 consists of detailed views of the tip cap and sleeve assembly of the instrument of FIG. 1, FIG. 9(a) being an end view, FIG. 9(b) being a side view partially in section, FIG. 9(c) being a front view and FIG. 9(d) being a detail of a corner indicated by circular arrow d in FIG. 9(b).
Figure 9B:
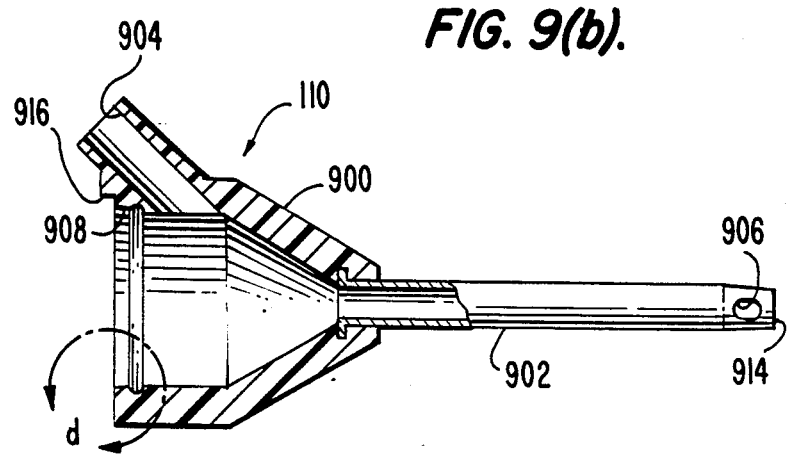
Figure 9C:
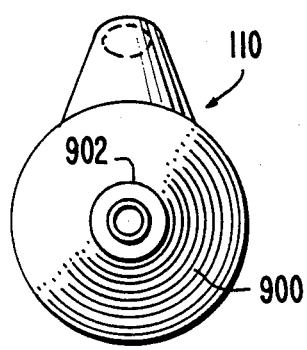
Figure 9D:
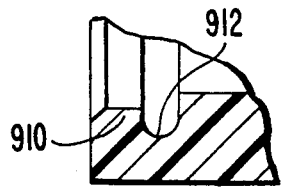

Piston 108 in a preferred embodiment comprises three parts. Male part 600 is depicted in FIG. 6, female part 700 is depicted in FIG. 7, and washer 800 is depicted in FIG. 8. Male part 600 is provided with a head 602 and stem 604. An outer wall 606 of head 602 defines longitudinally disposed groove 608, and axial bore 610 is molded into the part. The piston is composed of a suitable synthetic resin such as ABS such that axial bore 610 is radially distensible. The diameter of axial bore 610 is selected such that it is slightly smaller than an exterior diameter of inner tube 202, such that the inner tube is held by the piston by means of a press fit.

Female part 700 is generally cylindrical in shape and is also manufactured of a suitable synthetic resin such as ABS. The female part defines a bore 702 having a diameter slightly smaller than the diameter of stem 604 of the male part, such that the two parts are joined in a press fit. A bevelled edge 602 provided on stem 610 of the male part assists in the attachment.

The piston comprises washer 800 in order to sealingly engage an annular inner surface 122 of barrel 102. In a preferred embodiment, the seal is a washer made of a highly fluorinated synthetic resin such as a polytetrafluoroethylene. Outer periphery 802 has a diameter selected to sealingly engage inner surface 122, and inner periphery 804 is selected to fit around stem 604 of the male part. As illustrated in FIG. 1, washer 800 is positioned between the male and female parts before they are press fit together. In another embodiment, the piston is integrally formed with an annular groove into which an 0-ring is fitted. By virtue of the sealing engagement of washer 800 and rear cap 106 with the inner surface of barrel 102 a chamber 124 is defined between the washer and the rear cap.

In a preferred embodiment, inner tube 202 is slightly bent in a direction toward cutting orifice 214 of the outer tube, typically at an angle of about 2 to 3 degrees, at a region adjacent to the inner tube's distal end 204. By bending the inner tube in this fashion, additional pressure is applied in order to further assist in maintaining a proper meshing between cutting edges 208 and 216. The additional pressure also assists in providing a self-sharpening action of the cutting edges. In this embodiment, it is necessary to provide a suitable guide means in order to keep inner tube 202 from rotating with respect to outer tube 200. This is accomplished by virtue of the fact that inner tube 202 is held by piston 108, and piston 108 is restrained from rotational movement by virtue of the cooperation between longitudinal groove 608 of the piston and key 404 of the barrel. As can best be appreciated in FIG. 1, key 404 moves within groove 608 as piston 108 moves axially within barrel 102.

Before pressurized gas is introduced through inlet 508, into chamber 124, piston 108 is urged rearwardly by spring 126 which is disposed about inner tube 202 in spring chamber 310. The extent to which the piston is moved by the rearward urging is controlled by adjustment screw 114 which, at its tip 128, abuts a rear surface of the piston. By adjusting screw 114, the rearward extent of the reciprocating axial movement of the piston and inner tube 202 is varied.

When pressurized gas is admitted through inlet 508 into chamber 124, the pressurized gas exerts a forwardly directed force on the piston that is greater than the competing rearward force exerted by the spring causing the piston and inner tube to move forward. The piston and inner tube are caused to move axially forward and backward in a reciprocating fashion by intermittently applying pressurized gas.

As depicted in FIG. 1, a second chamber 130 is defined within barrel 102 between front cap 104 and piston 108. As described hereinabove, front cap 104 defines exhaust ports that extend from a surface in contact with the second chamber to an exterior surface of the front cap. Air that is in chamber 130 when pressurized air is supplied to chamber 124 is allowed to escape to the exterior environment through the exhaust ports.

When it is desired to provide a source of irrigation fluid to the interior of the eye, as for example in order to prevent collapse of the anterior chamber of the eye when the instrument is used therein, tip cap and sleeve assembly 110 is fitted over the outer tube. The tip cap and sleeve assembly is depicted in detail in FIG. 9. The assembly comprises tip cap 900 which is molded from a synthetic resin, for example a silicone resin, and in which is embedded sleeve 902. The internal diameter of sleeve 902 is selected such that it fits over outer tube 200. The tip cap defines an inlet 904 which is connected to a source of irrigation fluid, and the sleeve defines at least one laterally directed irrigation outlet 906 from which irrigation fluid flows into the surgical site. Annular opening 908 is provided at the rear of the cap and annular flange 910 defines a groove 912 adjacent to the annular opening.

The arrangement of flange 910 and groove 912 allows tip cap and sleeve assembly 110 to be press fitted onto front surface 306 of front cap 104. In this way, boss 308 disposed on stem 304 of the front cap is received within groove 912 after it passes through flange 910. When attached, distal tip 914 of the sleeve extends to a point adjacent to and rearward of second cutting edge 216. Irrigation outlet 906, being disposed adjacent to distal tip 914, is similarly situated adjacent to and rearward of the cutting edge.

Preferably, there are two diametrically opposite irrigation outlets and each are maintained in a 90° alignment with cutting orifice 214 by virtue of the provision of key 916 which is provided on a rear surface of tip cap 900. When assembled, key 916 is received within recess 318 defined within front cap 104, such that rotational movement of the tip cap and sleeve assembly with respect to the cutting orifice is prevented.

By selecting appropriate interior dimensions of the cap and sleeve, an annular channel is provided for conducting the irrigation fluid from inlet 904 to outlet 906. In the depicted embodiment, the interior dimensions of the cap allow for the flow of irrigation fluid over stem 304 of front cap 104. The internal diameter of sleeve 902 is greater than an external diameter of outer tube 200 in order to allow fluid to pass between the outer tube and the inner surface of the sleeve. At distal end 914, the diameter of the sleeve is reduced so that irrigation fluid passes through irrigation outlets 906 rather than the distal end.

Figure 10:
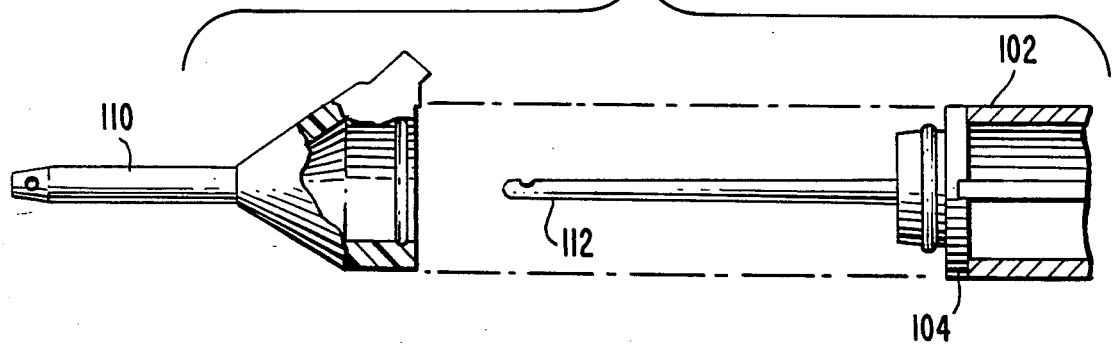
FIG. 10 is an exploded side view of the handpiece with the tip cap and sleeve assembly removed.

FIG. 10 shows the tip cap and sleeve assembly 110 disengaged from the front cap 104 and removed from the handpiece. The dashed lines show how the tip cap and sleeve assembly 110 is fitted over the outer cutter tube 112 and onto the front cap 104 of the handpiece.

Having thus described the invention in terms of a detailed embodiment, it will be readily apparent to those skilled in the art that many modifications and variations may be introduced without departing from the inventive scope of the present teachings.

What is claimed is:

1. An intraocular surgical instrument comprising:

a handpiece, an elongated inner tube movably connected at a first end to said handpiece and having a first cutting edge at a second end, an elongated outer tube disposed about said inner tube, and connected at a first end to said handpiece, and said first cutting edge sliding across said second cutting edge when said inner tube is moved axially relative to said outer tube, and said inner and outer tubes defining a first clearance therebetween at a first rearward region, a second clearance therebetween at a second region adjacent to said cutting edges, said first and second clearances maintaining said cutting edges in a cutting relationship, and a third clearance, larger than said first and second clearances, at a third region between said first and second regions.

2. The instrument of claim 1 including, said first region being disposed adjacent to said first end of said outer tube.

3. The instrument of claim 1 including, said first and second clearances being the same distances.

4. The instrument of claim 3 including, said first clearance being about 0.00025 inches.

5. The instrument of claim 1 including, said third clearance being about 0.003 inches.

6. The instrument of claim 1 including, said third clearance being about 0.002 to 0.003 inches.

7. The instrument of claim 1 including, said first and second clearances being provided by reduced internal diameters of said outer tube in said first and second regions, respectively.

8. The instrument of claim 1 including, a guide means for preventing rotational movement of said inner tube relative to said outer tube.

9. The instrument of claim 1 including, said first cutting edge defining a cutting orifice, and a suction means for sucking material into and through said cutting orifice, and through the interior of said inner tube.

10. An intraocular surgical instrument comprising:

a handpiece, an elongated inner tube movably connected at a first end to said handpiece and having a first cutting edge at a second end, an elongated outer tube disposed about said inner tube, and connected at a first end to said handpiece, said first cutting edge sliding across said second cutting edge when said inner tube is moved axially relative to said outer tube, said handpiece comprising a barrel, a front cap fitted into said barrel, said front cap defining an axial bore adapted to hold said outer tube and through which said inner tube passes, a rear cap fitted to said barrel and defining an axial bore through which said inner tube passes, a piston disposed between said front and rear caps and defining an axial bore through which said inner tube passes, a biasing means for urging said piston rearwardly towards said rear cap, and an exerting means for exerting a forwardly directed force on said piston greater than the rearwardly-urging force of said biasing means so as to move said piston forward towards said front cap.

11. The instrument of claim 10 including, said exerting means comprising a pressurized gas means.

12. The instrument of claim 10 including, said rear cap comprising a tapered outer wall having a diameter at a rearward end that is slightly larger than an interior diameter of said barrel, such that said rear cap is press fitted into said barrel.

13. The instrument of claim 10 including, a chamber defined between said piston and said rear cap, said rear cap defining a threaded bore, an adjustment screw adjustably positioned in said threaded bore, and said adjustment screw having an end extending a variable amount into said chamber and abutting a rear surface of said piston when said piston is rearwardly urged.

14. The instrument of claim 13 including, said exerting means comprising a pressurized gas means.

15. The instrument of claim 10 including, said front cap including a rearwardly projecting sleeve, said sleeve defining the outer boundary of a rearwardly disposed sleeve chamber, and said biasing means having a forward end thereof positionable in said sleeve chamber.

16. The instrument of claim 15 including said biasing means comprising a spring having its forward end engageable with said front cap at a location within said sleeve chamber.

17. The instrument of claim 15 including, said front cap including an exhaust passageway communicating with said sleeve chamber.

18. The instrument of claim 17 including, said passageway including an exit port at an outer surface of said front cap forward of said sleeve chamber.

19. The instrument of claim 17 including, said front cap having an outer wall, and said passageway extending longitudinally along said outer wall.

20. The instrument of claim 10 including, a tip cap assembly positioned forwardly of said front cap and supported at least in part by said handpiece.

21. The instrument of claim 20 including, said tip cap assembly having an inlet communicable with a source of irrigation fluid, an outlet for the irrigation fluid from the source of irrigation fluid, and an irrigation channel providing a fluid communication between said inlet and said outlet.

22. The instrument of claim 21 including, said outlet being directed laterally relative to the movement of said inner tube.

23. The instrument of claim 20 including, said tip cap assembly including a sleeve fitting over said outer tube.

24. The instrument of claim 23 including, said sleeve having a distal sleeve end disposed adjacent to and rearward of said second cutting edge.

25. The instrument of claim 24 including,
said outlet for the irrigation fluid being disposed adjacent to said distal sleeve end.

26. The instrument of claim 21 including,
a positioning means for positioning said outlet so it is oriented generally 90° relative to said second cutting edge.

27. The instrument of claim 26 including,
said positioning means comprising a key and a recess device attached to said tip cap assembly and to said front cap.

28. The instrument of claim 27 including,
said key fitting into said recess device.

29. The instrument of claim 20 including,
a retaining means for retaining said tip cap assembly on said front cap.

30. The instrument of claim 29 including,
said retaining means including an annular flange on said tip cap assembly and defining an annular groove, a stem attached to said front cap, said stem having an annular boss fitting within said annular groove to retain said tip cap assembly on said front cap.

31. The instrument of claim 10 including,
said barrel having a forward edge, and
said front cap being positioned generally entirely within said barrel between said forward edge and said rear cap.

32. The instrument of claim 10 including,
said first cutting edge defining a cutting orifice, and
a suction means for sucking material into and through said cutting orifice, and through the interior of said inner tube.

33. The instrument of claim 10 including,
a guide means for preventing rotational movement of said inner tube relative to said outer tube.

34. An intraocular surgical instrument comprising:
a handpiece having an interior wall,
an elongated inner tube movably connected at a first end to said handpiece and having a first cutting edge at a second end,
an elongated outer tube disposed about said inner tube, and connected at a first end to said handpiece,
said first cutting edge sliding across said second cutting edge when said inner tube is moved axially relative to said outer tube,
a guide means for preventing rotational movement of said inner tube relative to said outer tube,
said guide means comprising a key disposed on said interior wall and a piston having a wall that defines a longitudinally disposed groove,
said piston being connected to said inner tube and contained within said handpiece, and
said piston being adapted to move axially such that said key moves within said groove.

35. The instrument of claim 34 including,
said first cutting edge defining a cutting orifice, and
a suction means for sucking material into and through said cutting orifice, and through the interior of said inner tube.

* * * * *